United States Patent
Grajcar et al.

(10) Patent No.: US 9,433,194 B2
(45) Date of Patent: Sep. 6, 2016

(54) AQUACULTURE LIGHTING DEVICES AND METHODS

(71) Applicant: ONCE Innovations, Inc., Plymouth, MN (US)

(72) Inventors: Zdenko Grajcar, Crystal, MN (US); Michael J. Ostaffe, Maple Grove, MN (US)

(73) Assignee: ONCE Innovations, Inc., Plymouth, MN (US)

( * ) Notice: Subject to any disclaimer, the term of this patent is extended or adjusted under 35 U.S.C. 154(b) by 466 days.

(21) Appl. No.: 13/715,904

(22) Filed: Dec. 14, 2012

(65) Prior Publication Data

US 2013/0152864 A1 Jun. 20, 2013

Related U.S. Application Data

(60) Provisional application No. 61/570,552, filed on Dec. 14, 2011.

(51) Int. Cl.
*A01K 39/01* (2006.01)
*A01K 63/06* (2006.01)
(Continued)

(52) U.S. Cl.
CPC .............. *A01K 63/06* (2013.01); *A01G 33/00* (2013.01); *A01K 61/00* (2013.01); *A01K 61/005* (2013.01);
(Continued)

(58) Field of Classification Search
CPC .. A01K 61/00; A01K 61/005; A01K 61/006; A01K 63/042; A01K 61/007; A01K 61/001; A01K 61/02; A01K 63/00; A01K 63/04; A01K 63/06; A01K 63/045; A01K 67/00; A01K 69/00; A01K 75/00; A01K 79/02; F21V 23/04

USPC ........ 119/204, 215, 233; 362/230, 231, 234, 362/249.01, 249.02, 276
See application file for complete search history.

(56) References Cited

U.S. PATENT DOCUMENTS

| 2,709,984 A | 6/1955 | Marks | |
|---|---|---|---|
| 3,939,802 A * | 2/1976 | Neff | .......................... 119/51.04 |

(Continued)

FOREIGN PATENT DOCUMENTS

| CN | 1042039 A | 5/1990 |
|---|---|---|
| CN | 1280764 A | 1/2001 |

(Continued)

OTHER PUBLICATIONS

Notification of Transmittal of the International Search Report and the Written Opinion of the International Searching Authority issued in International Patent Application No. PCT/US2012/069379 dated Feb. 25, 2013.

(Continued)

*Primary Examiner* — Yvonne Abbott-Lewis
(74) *Attorney, Agent, or Firm* — McDermott Will & Emery LLP (57) ABSTRACT

A lighting assembly for enhancing the growth of aquatic life in an ecosystem and method of enhancing the growth of aquatic life in such an ecosystem. The assembly includes a vessel submerged within water of the ecosystem. A substrate is disposed within and surrounded by the vessel and provides electronics to provide a conditioned current to a plurality of light emitting diodes also contained on the substrate. The light emitting diodes emit light within the water of the ecosystem that provides for growth, not only in a larger volume of the ecosystem, but in addition enhances the growth of the aquatic life.

11 Claims, 7 Drawing Sheets

(51) Int. Cl.

| | | |
|---|---|---|
| *A01G 33/00* | (2006.01) | |
| *A01K 61/00* | (2006.01) | |
| *C12M 1/00* | (2006.01) | |
| *C12N 1/12* | (2006.01) | |
| *C12N 13/00* | (2006.01) | |
| *F21V 3/04* | (2006.01) | |
| *F21V 29/58* | (2015.01) | |
| *F21V 31/00* | (2006.01) | |
| *H01L 33/58* | (2010.01) | |
| *H01L 33/64* | (2010.01) | |
| *F21S 2/00* | (2016.01) | |
| *F21V 21/08* | (2006.01) | |
| *F21V 23/04* | (2006.01) | |
| *F21Y 101/02* | (2006.01) | |
| *F21Y 103/00* | (2016.01) | |

(52) U.S. Cl.
CPC ............ *C12M 21/02* (2013.01); *C12M 31/10* (2013.01); *C12N 1/12* (2013.01); *C12N 13/00* (2013.01); *F21V 3/0418* (2013.01); *F21V 3/0472* (2013.01); *F21V 29/58* (2015.01); *F21V 31/00* (2013.01); *H01L 33/58* (2013.01); *H01L 33/64* (2013.01); *F21S 2/00* (2013.01); *F21V 21/0824* (2013.01); *F21V 23/04* (2013.01); *F21V 23/0442* (2013.01); *F21Y 2101/02* (2013.01); *F21Y 2103/003* (2013.01); *H01L 33/648* (2013.01); *H01L 2224/48091* (2013.01); *H01L 2924/13091* (2013.01); *Y10T 29/4973* (2015.01)

(56) References Cited

U.S. PATENT DOCUMENTS

| | | | |
|---|---|---|---|
| 4,137,869 A * | 2/1979 | Kipping | 119/230 |
| 4,379,437 A * | 4/1983 | Knowles | 119/230 |
| 4,699,086 A * | 10/1987 | Mori | 119/51.04 |
| 4,699,087 A * | 10/1987 | Mori | 119/51.04 |
| 4,703,719 A * | 11/1987 | Mori | 119/51.04 |
| 5,027,550 A | 7/1991 | Mori | |
| 5,161,481 A * | 11/1992 | Laufer | 119/205 |
| 5,713,303 A * | 2/1998 | Willinsky et al. | 119/218 |
| 5,850,806 A * | 12/1998 | Mark et al. | 119/219 |
| 5,937,791 A * | 8/1999 | Baugher et al. | 119/219 |
| 6,203,170 B1 | 3/2001 | Patrick et al. | |
| 6,347,908 B1 * | 2/2002 | Safwat | 405/81 |
| 6,361,192 B1 | 3/2002 | Fussell et al. | |
| 6,421,952 B1 * | 7/2002 | Vascocu | 43/113 |
| 7,220,018 B2 * | 5/2007 | Crabb et al. | 362/234 |
| 7,800,119 B2 | 9/2010 | He et al. | |
| 7,845,814 B2 | 12/2010 | Crabb et al. | |
| 7,878,674 B2 | 2/2011 | Crabb et al. | |
| 7,906,793 B2 | 3/2011 | Negley | |
| 8,111,001 B2 | 2/2012 | Underwood et al. | |
| 2003/0222503 A1 | 12/2003 | Lam et al. | |
| 2005/0128751 A1 | 6/2005 | Roberge et al. | |
| 2005/0135104 A1 | 6/2005 | Crabb et al. | |
| 2005/0236998 A1 | 10/2005 | Mueller et al. | |
| 2007/0069663 A1 | 3/2007 | Burdalski et al. | |
| 2007/0176182 A1 | 8/2007 | Wen et al. | |
| 2007/0268693 A1 | 11/2007 | Thomas et al. | |
| 2007/0268702 A1 * | 11/2007 | McFadden | 362/294 |
| 2008/0273331 A1 | 11/2008 | Moss et al. | |
| 2009/0080187 A1 | 3/2009 | Chou | |
| 2009/0140668 A1 | 6/2009 | Crabb et al. | |
| 2010/0005711 A1 | 1/2010 | McNeff | |
| 2010/0045198 A1 | 2/2010 | Lee et al. | |
| 2010/0239441 A1 | 9/2010 | Bade et al. | |
| 2010/0268390 A1 * | 10/2010 | Anderson | 700/284 |
| 2011/0012157 A1 | 1/2011 | Shi | |
| 2011/0078949 A1 | 4/2011 | Schuster et al. | |
| 2011/0089830 A1 | 4/2011 | Pickard et al. | |
| 2011/0101410 A1 | 5/2011 | Lin et al. | |
| 2011/0209400 A1 | 9/2011 | Rooymans | |
| 2011/0279015 A1 | 11/2011 | Negley et al. | |
| 2011/0280011 A1 | 11/2011 | Crabb et al. | |
| 2011/0291135 A1 | 12/2011 | Hsieh et al. | |
| 2011/0303927 A1 | 12/2011 | Sanpei et al. | |
| 2011/0316014 A1 | 12/2011 | Hiroyuki | |
| 2011/0316420 A1 | 12/2011 | Chang et al. | |
| 2011/0317416 A1 | 12/2011 | Oyaizu et al. | |
| 2012/0013238 A1 | 1/2012 | Jonsson | |
| 2012/0044713 A1 | 2/2012 | Chiang et al. | |
| 2012/0098458 A1 | 4/2012 | Dai et al. | |
| 2012/0149091 A1 | 6/2012 | Wilkerson et al. | |
| 2012/0212129 A9 | 8/2012 | Chou et al. | |
| 2013/0027947 A1 | 1/2013 | Villard et al. | |
| 2013/0058103 A1 | 3/2013 | Jiang et al. | |

FOREIGN PATENT DOCUMENTS

| | | |
|---|---|---|
| CN | 1692700 A | 11/2005 |
| CN | 201344401 Y | 11/2009 |
| CN | 101868529 A | 10/2010 |
| CN | 201944685 U | 8/2011 |
| EP | 1610593 A2 | 12/2005 |
| EP | 2284440 A1 | 2/2011 |
| JP | 4241870 | 8/1992 |
| JP | 4241870 B2 | 3/2009 |
| JP | 2011134903 A | 7/2011 |
| JP | 4796027 B2 | 10/2011 |
| WO | 2005/109086 A1 | 11/2005 |
| WO | 2006/137741 A1 | 12/2006 |
| WO | 2009-066231 A2 | 5/2009 |
| WO | 2011/019288 A2 | 2/2011 |
| WO | 2011068843 A1 | 6/2011 |

OTHER PUBLICATIONS

U.S. Office Action issued in U.S. Appl. No. 13/715,884, filed Mar. 28, 2014.
International Preliminary Report on patentability issued in International Application No. PCT/US2012/069728 dated Jun. 17, 2014.
International Preliminary Report on patentability issued in International Application No. PCT/US2012/069379 dated Jun. 17, 2014.
Leah Jackson et al., "Aquaculture Research Center gets national attention for crawfish production", News Bureau, Northwestern State University, Jul. 7, 2011.
Janet McConnaughey, "La. researcher uses light to grow bigger crawfish", http://www.dailycomet.com/article/20110706/WIRE/110709753?template=printpicart, Jul. 31, 2014.
International Preliminary Report on patentability issued in International Application No. PCT/US2012/068701 dated Jun. 26, 2014.
U.S. Office Action dated Aug. 14, 2014 issued in U.S. Appl. No. 13/585,806.
US Office Action issued in U.S. Appl. No. 13/715,884 mailed Jul. 5, 2013.
US Office Action issued in U.S. Appl. No. 13/585,806 mailed Jan. 23, 2014.
Notification of Transmittal of the International Search Report and the Written Opinion of the International Searching Authority issued in International Patent Application No. PCT/US12/68701 dated Dec. 10, 2012.
Final Office Action issued in U.S. Appl. No. 13/715,884, dated Dec. 26, 2014.
Hongshan Su: "Fish Culture in Light Net Pen Underwater" (title also translated as "Test of Fish Farming in Underwater Lighting Cage"), Journal of Zoology, vol. 2, 1983, pp. 31-32, with English translation.
Office Action issued in Chinese Application No. 201280070124.6, dated May 18, 2015, with English translation.
Chinese Office Action issued in Chinese Application No. 201280067879.0 dated Apr. 1, 2015, with English Translation.
U.S. Office Action issued in U.S. Appl. No. 13/585,806 dated Sep. 11, 2015.
U.S. Office Action issued in U.S. Appl. No. 13/715,884 dated Jun. 19, 2015.

* cited by examiner

AQUACULTURE LIGHTING DEVICES AND METHODS

CROSS REFERENCE

This application claims benefit to and is based upon U.S. Provisional Patent Application Ser. No. 61/570,552 filed Dec. 14, 2011 entitled LED Lighting Structures and that application is incorporated by reference in full.

BACKGROUND

This invention is related to LED Lighting Assemblies. More specifically, this invention relates to an underwater LED lighting assembly for enhancing aquaculture in natural and man-made ecosystems.

Lighting can be used to affect the growth of aquatic animals. Specifically, light is needed for growth of most animal species and substantially affects the animals' behavior in terms of feeding, reproducing, location in the water column, and other factors. Water naturally filters light as the water gets deeper, such that lower light intensity and a different spectrum of light wavelengths reaches deep water.

In aquaculture, carbon dioxide ($CO_2$) and oxides of nitrogen contaminate the water and create an environment that is lethal to certain animals. In nature, algae in the water can consume both $CO_2$ and nitrogen in the course of algae growth and photosynthesis; in so doing, the algae decontaminates the water while providing food to the animals. In order to use algae for such purposes, however, light needs to be present at proper frequencies and intensities to allow the algae to grow using photosynthesis. The quantity of light available in a water pond may be reduced by: 1) less than ideal periods of sunlight being present during a 24 hour solar cycle to permit photosynthesis to take place as may be desired; 2) the reflective nature of the water surface, which reflectance reduces the beneficial effect of available light on photosynthesis, and which reflectance changes as the angle of the sun to the water moves from acute to oblique as the day progresses, thus inhibiting photosynthesis, and 3) the fact that water containing high levels of solids (whether in the form of decaying or living matter, such as decaying or living algae) does not permit light to reach much beyond the surface. When the light in a water pond is reduced, photosynthesis can be reduced or become impossible, and the benefits of photosynthesis may be absent at any depth much below the surface. As such, the use of deeper water levels in aquaculture facilities may prove to be problematic.

Small ponds have several factors which inhibit light penetration into the pond, including lack of wave action, as the smaller body of water is more protected and picks up less wind energy. Without wave action, more light is reflected off of the surface of the water and does not penetrate into the pond (in contrast, with constant wave action, the sun's rays are only reflected a portion of the time and less of the sunlight is reflected as the continuously changing surface does not create a smooth reflective surface). Some measurements estimate that on a smooth surface pond, only 40% of the light energy penetrates the surface of the water. After a certain point, beyond the critical angle, all of the light is reflected off the surface and it becomes dark underwater (although it is still light above the water).

Protection also reduces the clearing of the water surface, and algae or other materials may come to rest on the surface and cloud the surface, which otherwise might have been blown from the surface of the pond and/or dissipated into a larger body of water. The animals may need to have different spectra of light passed to them for different depths of water. For example, a fish whose habitat is within a one meter depth from the surface of a pond may thrive with a different light spectrum than a fish whose habitat is deeper within the pond (e.g., at a depth of 10 meters).

Further, studies have shown that different living organisms are both physiologically and psychologically affected by the wavelength of light they receive. This holds true whether the living organism is a plant or animal as is discussed in several patents by the present inventor, including provisional patent application 61/669,825 entitled Light Sources Adapted to Spectral Sensitivity of Plants to Grajcar and 61/698,074 entitled Aquatic System for Manipulating Psychological and Physiological Effects in Aquatic Life to Grajcar, both that are incorporated in full herein.

Thus, a need in the art exists for an underwater lighting assembly that can be used to enhance and grow aquatic life in its natural habitat and also in man-made facilities. Further a need in the art exists to increase the yield, size and capacity for aquatic life.

Therefore, a principle object of the present invention is to provide a submergible LED lighting assembly for aquatic life;

Yet another object of the present invention is to optimize the growth and yield of aquatic life.

Another object of the present invention is to provide additional locations in which aquatic life can be grown for harvesting.

These and other objects, features and advantages will become apparent from the specification and claims.

SUMMARY OF THE INVENTION

A lighting assembly for enhancing the growth of aquatic life in an ecosystem and method of enhancing the growth of aquatic life in such an ecosystem. The assembly includes a vessel submerged within water of the ecosystem that contains a substrate disposed therein. The substrate has driving circuitry thereon to supply current to a plurality of light emitting diodes electrically connected to the driving circuitry. The light emitting diodes emit light within the water of the ecosystem that provides for growth, not only in a larger volume of the ecosystem, but in addition enhances the growth of the aquatic life.

The assembly can also include a control system, anchoring system and cleaning system for enhancing the performance of the assembly. In addition, the assembly provides both light duration and color or spectra control to allow a user to optimize the lighting output based on predetermined attributes of the aquatic life and ecosystem to optimize yield and growth of the aquatic life.

DETAILED DESCRIPTION OF A PREFERRED EMBODIMENT OF THE INVENTION

The figures show a lighting assembly 10 to be used in an ecosystem 12 that can be either naturally occurring or a natural ecosystem created outdoors in nature, or a man-made ecosystem created indoors. For example, the naturally occurring ecosystem can include a pond, creek, lake, man-made waterway, river, sea, ocean or the like that receives direct lighting from the sun. A man-made ecosystem is one made indoors or within a dwelling, and is either an aquarium, or other indoor aquatic breeding structure that does not directly receive lighting from the sun. Instead, lighting is provided only through windows, interior lighting or the like.

The lighting assembly 10 is a light source capsule that in one embodiment has a capsule or vessel 14 that in one embodiment extends from a closed first end 15a to an opened second end 15b. In a preferred embodiment the vessel 14 is a glass tube. In another embodiment the vessel is square or other shape and made of a clear material to allow the passage of light. The vessel in another embodiment can be made of a material or color, or alternatively have a coating that diffuses light, changes the color of light or materially alters light disposed therethrough.

Figure 4:
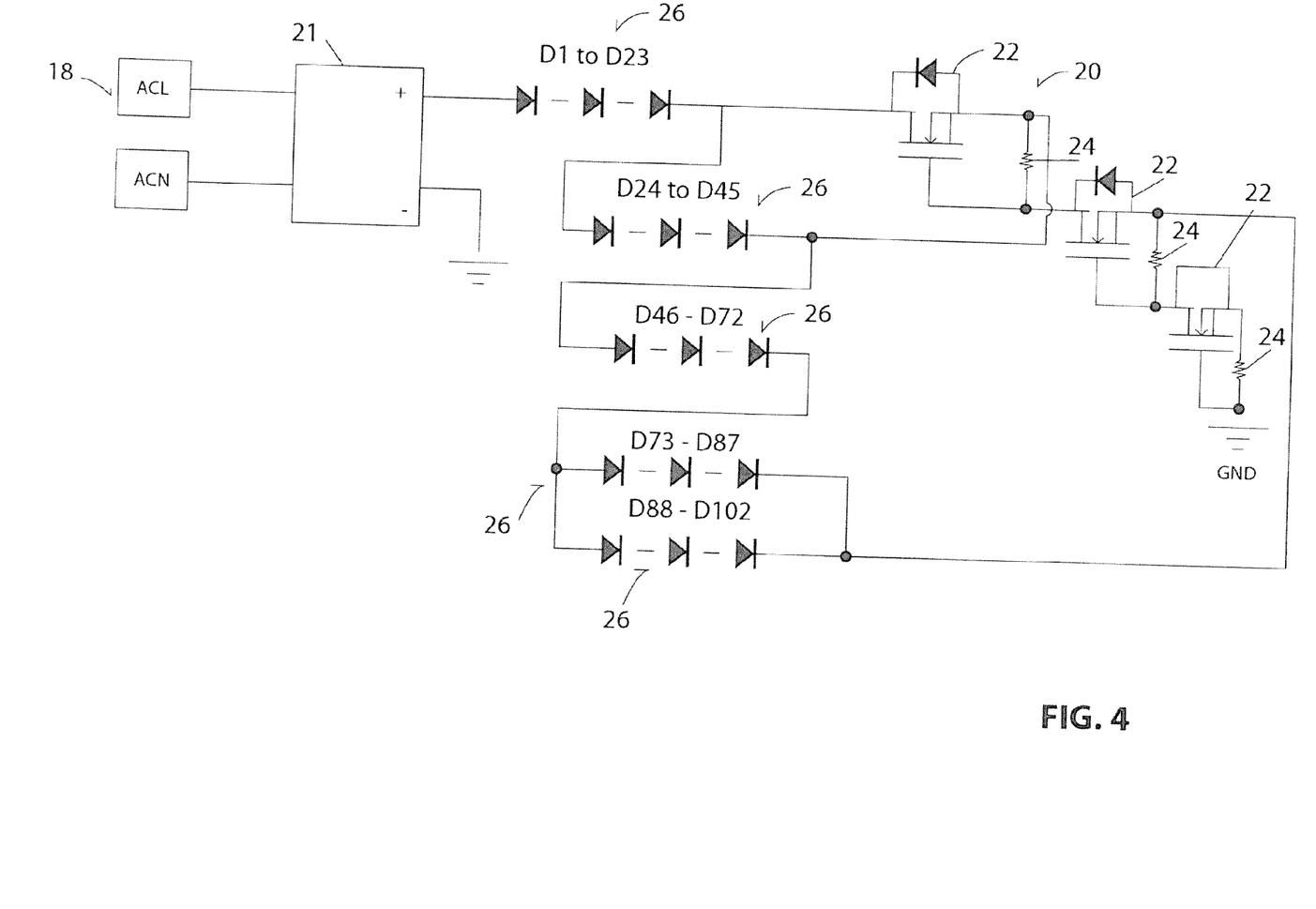
FIG. 4 is a schematic diagram of a lighting assembly for use in an ecosystem.

The vessel 14 surrounds and encloses a substrate 16 that can be of any size or shape. In one embodiment the substrate 16 is rectangular in shape and elongated the length of the vessel. In a preferred embodiment the substrate is a printed circuit board (PCB). Electrically connected to the substrate 16 is a power input 18 that in a preferred embodiment is an AC input and in another embodiment is a DC input. The input current is conditioned by driving circuitry 20 that includes a rectifier 21, at least one transistor 22 and a resistor 24. Protection circuitry such as a fuse or MOV also can be provided as needed. The driving circuitry conditions current for a plurality of light emitting diodes 26. The light emitting diodes 26 can be arranged in series, in series with the driving circuitry 20, in parallel, in parallel with the driving circuitry 20 or in any manner to produce light based on the power input 18 provided, whether AC or DC. In a preferred embodiment the driving circuit 20 and LEDs 26 are arranged as taught in U.S. Patent Pub. No. 2011/0210678 to Grajcar that is incorporated fully herein.

A medium 28 is disposed within the vessel 14 that surrounds the substrate 16. In one embodiment the medium 28 is a fluid and preferably is mineral oil. However, the fluid within the capsule 10 may be selected based on a variety of factors, including specific gravity of the material (e.g., less than the buoyancy created by air in the capsule), heat conductivity, and transparency to light at different wavelengths. The fluid (e.g., oil) within the capsule 14 may thus be selected to maximize heat transfer, to have a specific molecular weight, and/or to have a particular composition.

The medium 28 in one embodiment is clear to allow the passage of light therethrough, though the medium may be altered to be different colors or to have different characteristics to alter the light emitted by the LEDs 26 in order to create different color or wavelengths of light being diffused and emitted from the vessel. The main function of the medium 28 is to transfer heat from the driving circuitry 20 and LEDs 26 to the vessel 14 and thus to the water of the ecosystem 12.

An end cap 30 is removably secured to the opened second end 15b of the vessel 14. Specifically the end cap 30 is of size, shape and design to enclose the opened second end 15b in a sealing manner to prevent seepage of the medium 28 into the water of the ecosystem 12 while preventing water and contaminants carried therein from entering the vessel 14 and damaging the electronics and circuitry 16, 18, 20, 21, 22, 24 and 26. Simultaneously the end cap 30 has electrical wiring 32 disposed therethrough to provide electrical connection between the electronics and circuitry 16, 18, 20, 21, 22, 24 and 26 and an external power source 34. The end cap 30 is designed to provide a sealing connection between the end cap 30 and wiring 32 again to prevent water and contaminants from entering the vessel 14.

Figure 5:
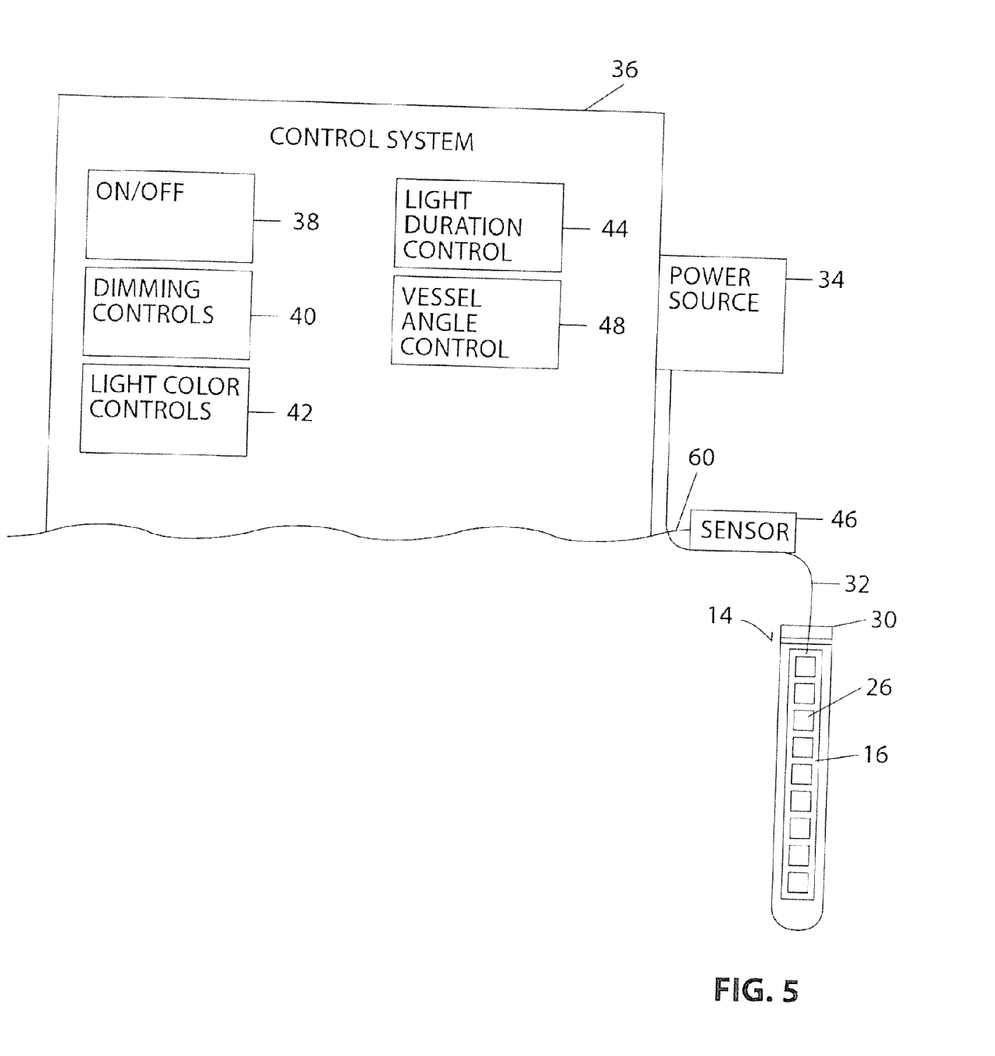
FIG. 5 is a schematic diagram of a lighting assembly with a control assembly for use in an ecosystem.

A control system 36 is electrically connected to the electrical wiring 32 to provide a user interface to control the operation of the LEDs 26. The control system includes, but is not limited to an on/off switch 38, dimming controls 40, light color controls 42 that in one embodiment is a function of the dimming controls 40 and flicker or light duration control 44 that controls the duration of light emitted by the LEDs 26.

Thus, the lighting assembly 10 optionally has different, independently controllable LEDs 26 so that light having different wavelength spectra can be produced at different positions along the light fixture or light assembly 10 (e.g., different spectra can be produced by lights located at different depths, different spectra can be produced by lights located at different locations, different spectra can be produced depending on a time of day, time of year, or ambient natural light reaching a particular depth in a pond, or the like).

The color of the lights inside the tube or vessel 14 are selected depending on the species of fish or shell fish to be influenced. Different colors affect the growth of different algae or aquatic animals. Adjusting the spectra of lighting can also compensate for differences in latitudes (how much light is reflected, on average, is a function of latitude), incident light on water of an ecosystem 12 such as a pond (e.g., whether the pond is outside under natural light or under a roof), or other factors. For ponds of differing depths, the LEDs 26 may be arrayed from the surface of the pond to the bottom of the pond. At different depths, the light intensity and color may be varied.

For example, outdoor ponds may have lighting designed to supplement or augment the natural lighting incident on the pond. Thus, at the surface of the pond during daylight, less light intensity may be required to be produced by the light fixture, and the light provided may only supplement the spectra filtered by the water. Deeper into the water, more light intensity may be needed and a broader spectra lighting may be needed to provide more broad spectra due to the filtering of the water.

Normally, algae only grow near the surface of the pond because that is where the light that is necessary for growth (photosynthesis) is available. By using additional lighting (including lighting directly within the pond), the lighting assembly 10 can increase the volume of water exposed to light by creating shafts where the light reaches deeper, thus allowing the algae to also grow along the length of the light tube or around the light point source deeper in the water—adding sunlight to more of the water.

The light spectra or intensity may alternatively or additionally be adjusted throughout the circadian day. For example, using independently controllable LEDs 26 arrayed from the surface of the water to the bottom of a pond, or alternatively at a point source (e.g., a single light fixture)

within the pond, the intensity and spectra of the light can be adjusted throughout the day. For lighting fixtures or assemblies 10 located closer to the surface, the fixtures may not need to be on during a sunny day (or may have their lighting intensity or spectra adjusted). However, on a cloudy day, in the morning or evening (e.g., at times when greater light is reflected off the surface of the water due to the angle of the sun being low and approaching the critical angle of the water) or at night, the intensity and spectra can be adjusted, for example to increase the brightness and/or spectra adjusted to compensate for different colors of light not penetrating into the water.

For such purposes, a lighting system or assembly 10 may include one or more light sensors 46 electrically connected to the control system 36. In one embodiment the sensors 46 are located at the surface of the water of the ecosystem 12 such as a pond or within the pond, and which are used to measure a natural light intensity and/or spectrum and adjust the lighting intensities and/or spectra of lighting fixtures in the system.

A vessel angling control 48 additionally can be part of the control system 36 that causes mechanical movement of the light assembly 10 to be directed at different angles in the water of an ecosystem 12 or pond. Adjusting for the direction of the light, the light can be adjusted to shine "down" or towards a deeper part of the pond (for example, to stimulate the growth of oysters, clams or scallops), to shine across or towards parts of the pond having similar depths as the light (to influence fish), or to shine up or towards the surface of the pond (for creatures which tend to feed on the surface, like frogs). The directional adjustments may also be performed using a Fresnel or other light directing materials/ constructs to direct light in a specific direction.

Figure 1:
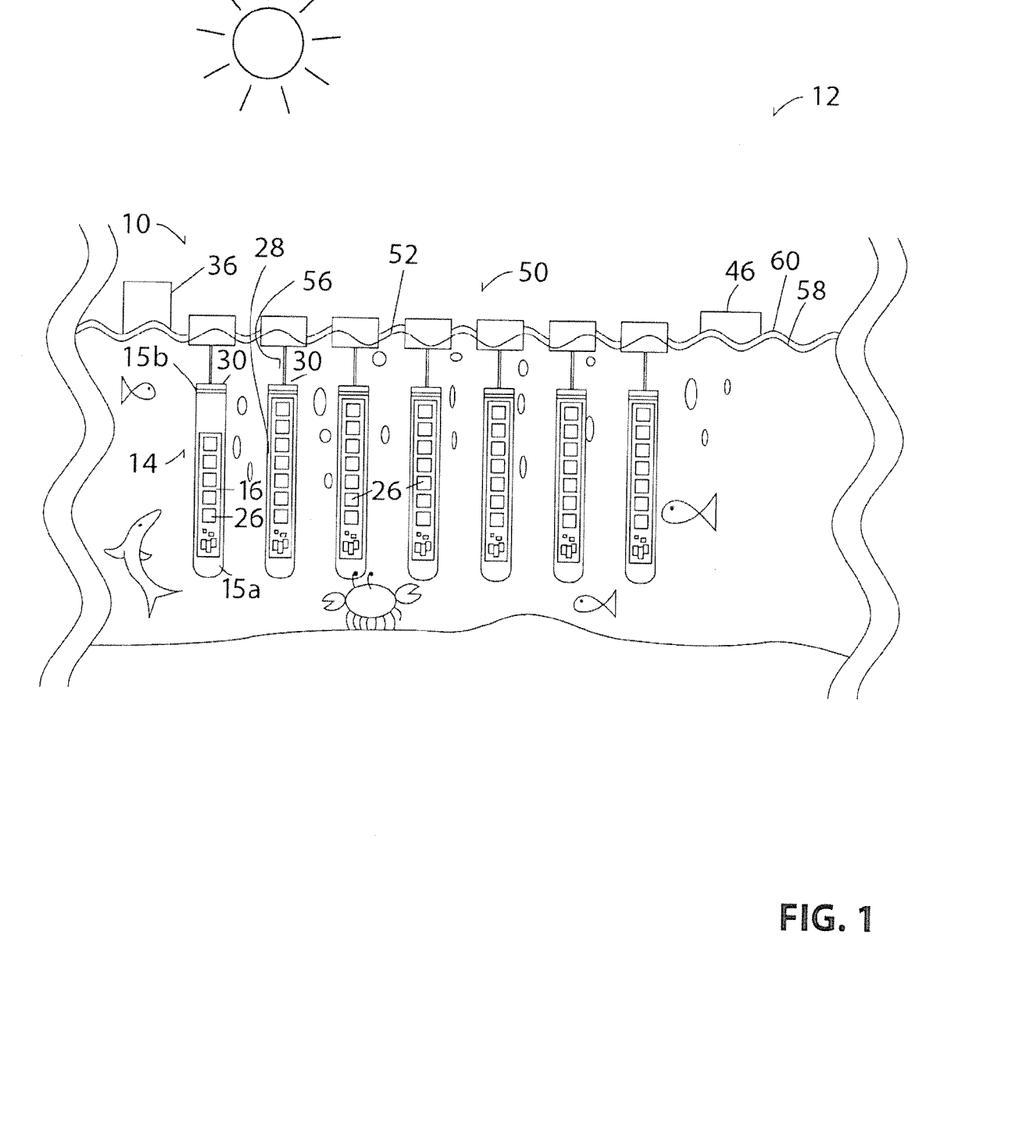
FIG. 1 is a side plan view of a lighting assembly within an ecosystem.

An anchoring system 50 in one embodiment suspends the lighting assemblies 10 from the surface of the water. Lighting fixtures or assemblies specifically hang from a floating mesh 52. The mesh 52 floats at or near the surface of the pond, and provides a two dimensional matrix from which light fixtures 10 hang into the water. The light fixtures 10 in one embodiment are configured to be heavier than water (or to be weighed), so as to sink in water and into the pond or other ecosystem 12 and be suspended from the floating mesh 52 with a suspension system 54. Multiple light fixtures 10 can be connected along a single cable or suspension member 56 originating from a point on the floating mesh, such that the lighting assemblies 10 provide light at multiple different depths below the origination point.

In another embodiment the lighting assemblies 10 hang from the floating mesh 52 in the water. The suspension member 56 such as cables and/or cords set the depth of the lighting assembly 10. In one embodiment the suspension system 54 includes a cable retraction/retention mechanism 58 and/or a power cord 60. The retraction/retention mechanism 58 (if the power cord 60 is also bearing the weight of the lighting apparatus) floats or holds the excess cable/power cord 60 to allow the length to be adjusted up or down. The wiring 32 that powers the lighting assembly 10 in one embodiment makes up part of the mesh 52 that holds the suspended lighting assemblies 10 in position.

Alternatively, the mesh 52 does not float and instead sinks or is anchored at or near the bottom of the pond, provided a two dimensional matrix from which light fixtures 10 can float up in the water. The light fixtures 10 are configured to be lighter than water, which in one embodiment is accomplished by connecting the vessel 14 to a floating device 62 or floater, so as to float up the vessel 14 in the water and thus anchored by the mesh 52.

Figure 2:
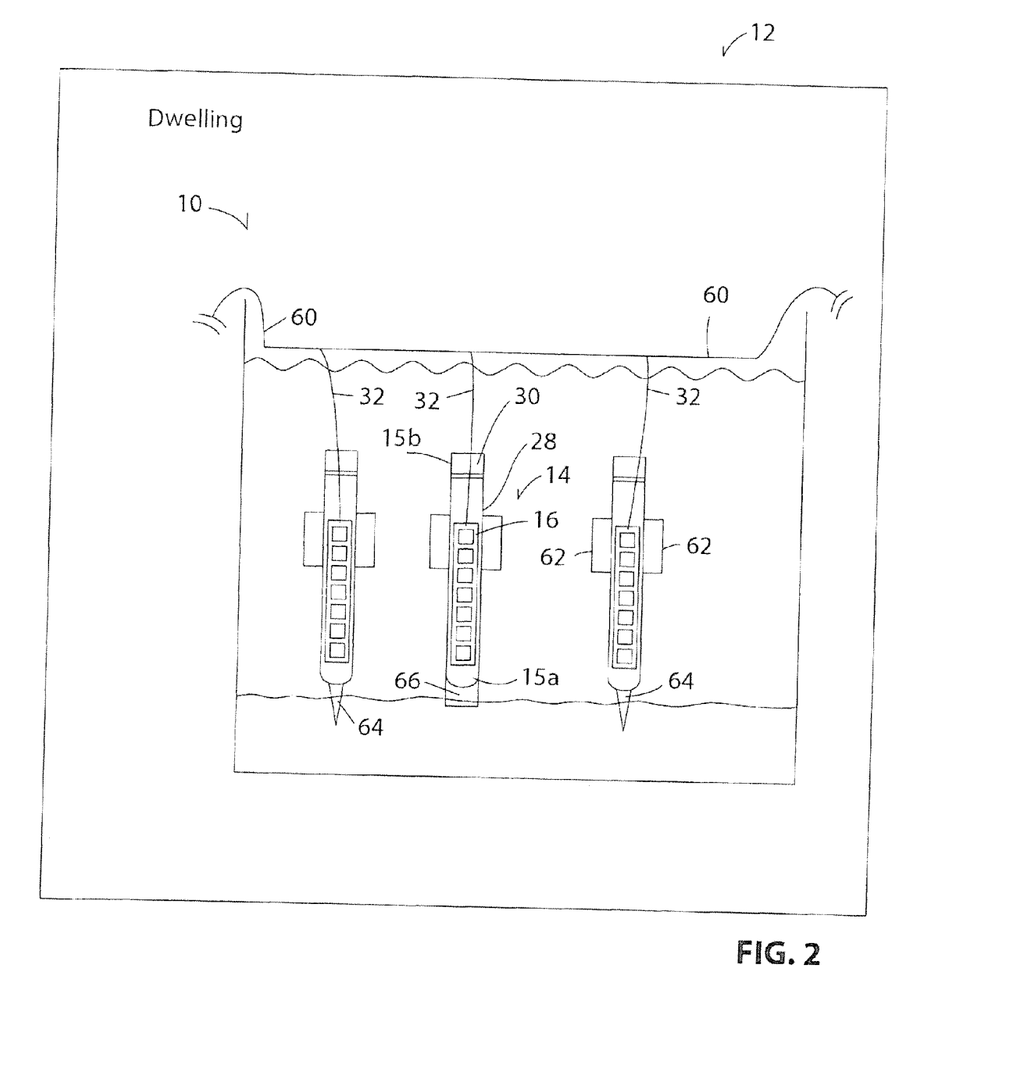
FIG. 2 is a side plan view of a lighting assembly within an ecosystem.
Figure 3:
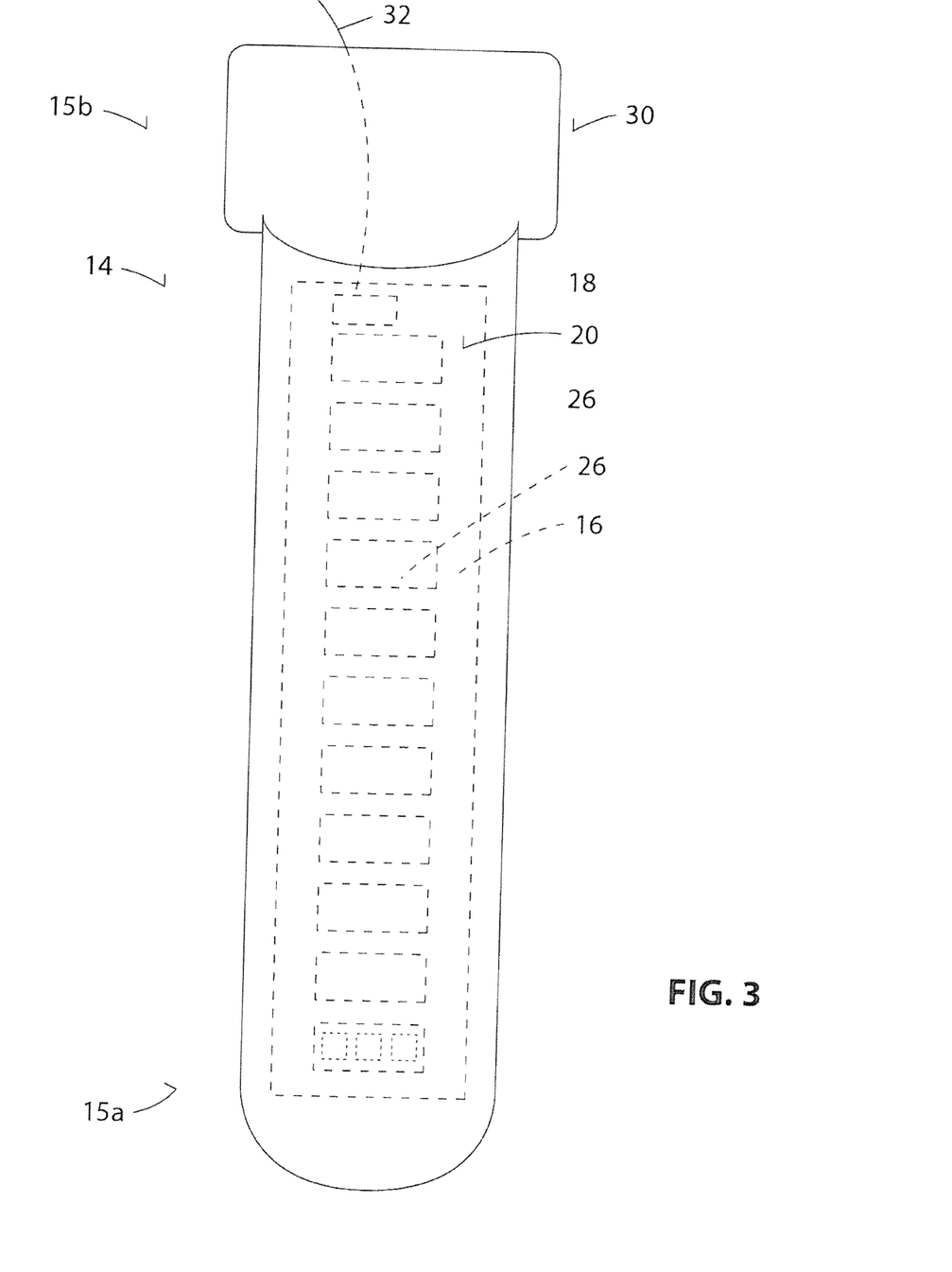
FIG. 3 is a perspective view of a lighting assembly for use in an ecosystem.

Alternatively, the light fixtures 10 are mounted on a stake 64 or other support that sits on the bottom of the pond and holds the light figures at specified distances above the bottom of the pond. Multiple light fixtures 10 are connected along a single cable/stake 64 originating from a point on the mesh 52 (e.g., the light fixtures may be provided at regular 1 meter intervals along the cable/stake 64), such that the light assemblies 10 provide light at multiple different depths above the origination point. In one embodiment the stake 64 is telescoping, which allows the vessel to be positioned at the specific depth of the water of an ecosystem or pool is being maintained and/or allows the lighting to be adjusted as the depth of the pool varies due to any number of reasons, such as environmental reasons.

Alternatively the vessel 14 is simply staked to the bottom of the pond. To avoid puncturing a pond liner, the vessel 14 is on, part of or secured to a standard 66 resting on the bottom of the pond (on the liner, for example). Where standards 66 are used instead of stakes to support the lighting in the water, the standards 66 also play a secondary role of providing habitat to aquatic animals. For example, the standards 66 are optionally designed to provide a variety of underwater structures and overhangs that may be used by aquatic animals seeking shelter.

Alternatively, top lights, if exposed during a drought or low water conditions can be independently controlled (turned off) to reduce energy use. The light assembly 10 rests on a light pole which does not penetrate or damage the liner. The wiring can simply rest along the floor (or may be suspended like wiring between telephone or power poles). A light assembly 10 can adjust the color spectra, or wavelength of the light. The light has different spectra which can be selectively activated to promote growth of different algae, animal species, etc.

Figure 6:
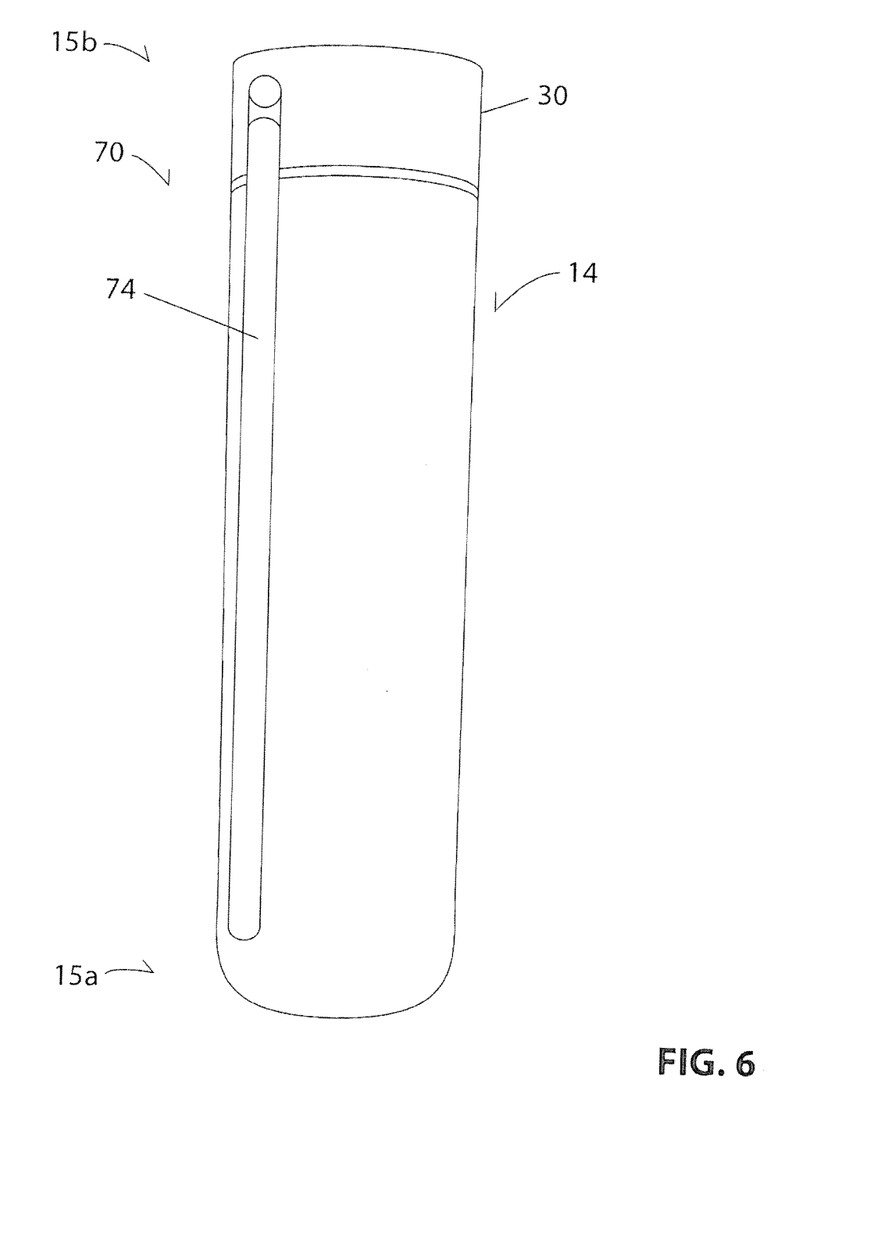
FIG. 6 is a perspective view of a lighting assembly with a cleaning assembly.

Optionally, a cleaning system 70 is provided for the vessel 14. In one embodiment a layer 72 of bio-fouling substance is applied to the surface to the lighting assembly 10 (such as a bio-fouling substance which prevents algae growth on the lighting figure, but does not affect aquatic animals). The bio-fouling substance or treatment may be applied to the surface to the submerged lighting fixture 10 in order to prevent (or retard) the growth and/or attachment of organisms to the fixture. The bio-fouling substance may be a simple silver emitting material, a surfactant, a hydrophobic material, or any other appropriate material or surface treatment. In one example, a material or treatment generally used to prevent algae growth in swimsuits and/or on the bottom of boats is used to reduce growth on submerged items.

Figure 7:
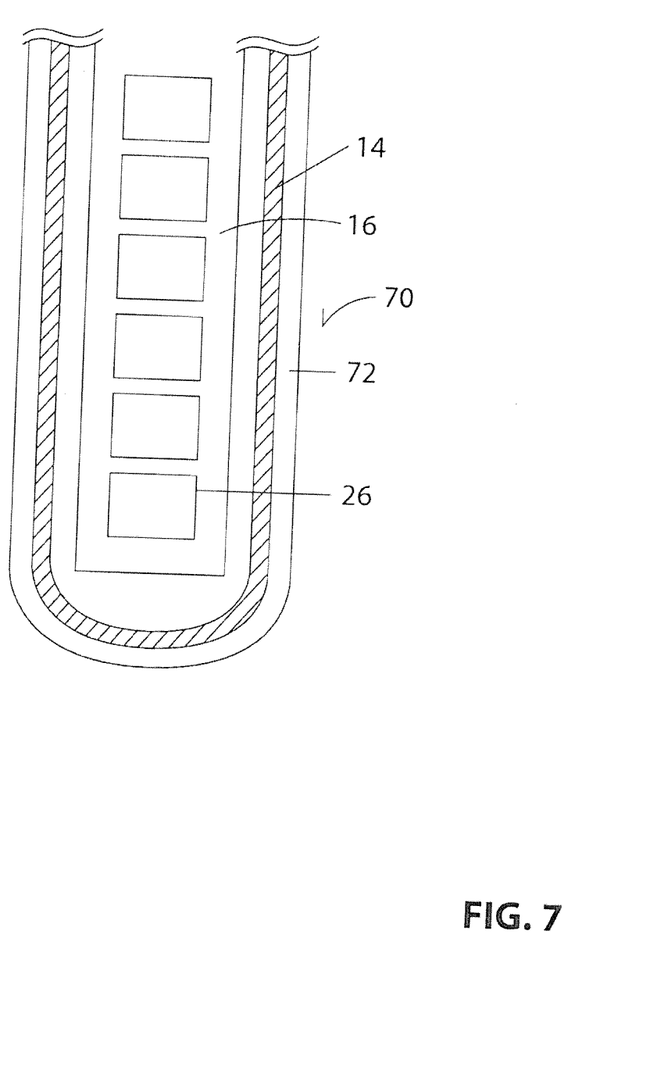
FIG. 7 is a sectional view of a lighting assembly with a cleaning assembly.

Alternatively the cleaning system 70 is a mechanical wiper 74 used to keep the light transmission area (e.g., a window or surface area through which the light is transmitted) clear of growth. The wiper is secured to the vessel 14 and functions to clean the exterior of the vessel as a result of the movement of the wiper 74 along the exterior of the vessel 14.

In operation the lighting assemblies 10 are placed in water of a predetermined ecosystem 12. The assemblies are positioned in a predetermined position in the water by an anchoring system 50. In particular, in one embodiment the assemblies are secured to mesh 52 and placed in the water to optimize the growth of aquatic life within the ecosystem 12. The assemblies 10 are then turned on by using the control system 36 that controls the coloring, intensity, light duration and angular position of the assembly 10 to be adjusted based on the predetermined aquatic life within the ecosystem 12 to maximize the growth, yield and physical makeup of the predetermined aquatic life within the ecosystem 12.

Thus presented is the ability to provide spectra-compensating illumination at a variety of depths in order to encourage and enhance the growth of aquatic animals and/or algae. The color/wavelength spectrum provided may be adjusted based on a variety of factors, including the natural illumination available at the chosen depth, the wavelength spectrum of natural light that is generally found at the chosen depth, the particular needs of the aquatic animals and algae, or the like.

Specifically, spectra-compensating illumination is designed to adapt to animal need. Therefore, the optimum lighting conditions, such as light color/wavelength, intensity and duration is predetermined for each animal and the type of algae that is in a predetermined ecosystem 12. Once the effects on animal behavior and algae is understood, the lighting assembly can either be specifically manufactured to present an assembly having the spectra, intensity and duration needs of the ecosystem or a lighting assembly 10 can be controlled by the control system 36 to provide this output. In this manner the most beneficial of those spectra and conditions is used to further enhance and optimize output of the system used to breed and raise the aquatic animals.

This also includes the concept of accelerating or regulating algae growth. When light is introduced into non-circulating water which has a high nitrogen/$CO_2$ concentration, the light accelerates algae growth, growth that consumes the $CO_2$ and nitrogen. The light may thus be used to reduce the $CO_2$/nitrogen (nitrites) concentration, by encouraging the consumption of the $CO_2$ and nitrogen by algae. As such, lighting assemblies 10 act as an apparatus that is used to lower and/or regulate the $CO_2$ and nitrogen levels in aqua ponds, so as to increase the oxygen levels in the aqua ponds.

The frequencies/wavelengths of sunlight that produce (or permit, cause, enhance, encourage, or favor) photosynthesis can be filtered out by the water and algae found in a pond, such that photosynthesis may not occur deep in the pond. The lighting assemblies 10 may thus be provided that are tunable to produce the frequencies/wavelengths of light required for photosynthesis in water regardless of water depth, sunlight penetration, etc. The lighting assemblies 10 increase the exposure of algae to light by exposing the algae to more photons. The light can be introduced directly into the water to avoid any of the light being reflected from the surface of the water, and thus avoid any reflection of light incident on the water surface at an angle exceeding the critical angle. The light can be used to promote algae growth, and can form part of an apparatus to get the nitrogen and/or $CO_2$ out of the water. The light can alternatively (or additionally) be provided from above the water.

Plants such as algae also require a dark period and individual plants each have an optimum light and dark duration or period. This is discussed further in U.S. Provisional Patent Applications No. 61/698,074 that has already been incorporated in full into this application. By using the light duration control 44 of the control system 36 this period may be predetermined and individual assemblies controlled to produce this duration as described in full in the '074 application. Thus algae production is maximized based on predetermining the type of algae presented and its reacts to different lighting parameters and then manufacturing the assembly to meet these parameters or setting an assembly via the control system 36 to meet these parameters.

In addition to applications in aquaculture, the light may be used in other applications to promote algae growth and/or the scavenging or consumption of Nitrogen/$CO_2$. For example, the light may be used in water treatment plants, wastewater treatment applications, pond cleaning applications, or the like.

Also presented is an assembly and method that improves animal growth, which feed on algae, which need light/nitrogen to grow. Therefore, in order to improve animal growth, lighting is used to control the amount of algae available to the animals at different depths and locations.

The lighting assemblies 10 also attract insects to the water surface. The underwater lighting assemblies 10 can also be used to attract insects to the surface of the water, and the insects can then be eliminated by natural biological processes (drowning, decomposition, and or eating). Thus additional food sources are provided.

Further, because of features such as filling the vessel 14 or capsule with a type of medium 28 such as fluid, like mineral oil, multiple LED devices 26 may be placed within a heavy weight glass tube or other vessel 14 and function efficiently. Specifically, the medium oil transfers heat from the LED devices and drivers (or other circuits) to the glass and then to the water. The combination of glass and oil allows the light sources to be cooled into the ambient water, thus enabling the light sources to be run at much higher light outputs (or at higher power levels) than if they were other types of lights or if the tube were filled with air and prevents overheating of the circuitry.

In sum, LEDs 26 located underwater may be used to resolve some or all of the problems discussed. The assemblies 10 can be installed at any economically reasonable depth, such that the growth and presence of beneficial algae at the installed depth becomes possible notwithstanding the presence of light-blocking contamination covering the LEDs or simply the depth of the water. In order to provide maximal algae growth in an ecosystem 12 such as a pond, a lighting system 10 for the pond includes lights arrayed throughout the pond. The lights 10 are distributed throughout the pond, so as to include lights located at different locations within the volume of the pond (e.g., to include lights at different locations of the footprint of the pond and at different pond depths). The orientation and/or grid of light fixtures can be of different sizes and dimensions depending on the depth of the growing pool or pond, the shape of the pool or pond (along a natural coast line, for example), type of water (salinity or opacity), or the size of the growing space. In this manner and as described above the lighting assemblies 10 can be tailored to any ecosystem 12 and type of aquatic life to be grown and either manufactured or actuated to provide an optimized growing based on the use of light. Thus, at the very least, all of the stated objects have been met.

What is claimed:

1. A method of enhancing the growth of aquatic life within a natural ecosystem comprising steps of:
    submerging a vessel within water of an natural ecosystem, said vessel having at least one light emitting diode;
    emitting light from the at least one light emitting diode such that the light is received by aquatic life in the natural ecosystem,
    predetermining the depth at which the at least one light emitting diode will be placed in the water; and
    predetermining the optimum wavelength of light to emit an optimum wavelength of light or an aquatic life based on the predetermined depth.

2. The method of claim 1 wherein the natural ecosystem is a pond.

3. The method of claim 1 further comprising the step of directing the at least one light emitting diode toward the bottom of the natural ecosystem.

4. The method of claim 1 further comprising the step of anchoring the vessel within the water.

5. The method of claim 1 wherein the light is emitting periodically.

6. The method of claim 1 wherein the aquatic life is algae.

7. The method of claim 1 wherein the aquatic life is a crustacean.

8. The method of claim 1 wherein the aquatic life is fish.

9. The method of claim 1 further comprising the step of increasing the intensity of the emitted light to enhance growth within the natural ecosystem.

10. The method of claim 1 further comprising the step of:
   predetermining the optimum wavelength of light of a predetermined aquatic life; and
   emitting light at the optimum wavelength.

11. The method of claim 1 wherein the emitted light attracts insects to the surface of the water.

\* \* \* \* \*